United States Patent [19]

Tilles

[11] 4,119,431

[45] Oct. 10, 1978

[54] HERBICIDAL EFFECT OF A MIXTURE OF CIS AND TRANS ISOMERS OF S-ISOPROPYL-1-(5-ETHYL-2-METHYL-PIPERIDINECARBOTHIOATE)

[75] Inventor: Harry Tilles, El Cerrito, Calif.

[73] Assignee: Stauffer Chemical Company, Westport, Conn.

[21] Appl. No.: 754,485

[22] Filed: Dec. 27, 1976

Related U.S. Application Data

[62] Division of Ser. No. 617,908, Sep. 29, 1975, abandoned.

[51] Int. Cl.$^2$ .............................................. A01N 9/22
[52] U.S. Cl. ...................................................... 71/94
[58] Field of Search ........................................... 71/94

[56] References Cited

U.S. PATENT DOCUMENTS 3,066,020   11/1962   Tilles et al. .............................. 71/94

FOREIGN PATENT DOCUMENTS 1,236,875   6/1971   United Kingdom ........................ 71/94

*Primary Examiner*—Catherine L Mills
*Attorney, Agent, or Firm*—Joel G. Ackerman

[57] ABSTRACT

A mixture of cis and trans isomers of S-isopropyl-1-(5-ethyl-2-methylpiperidinecarbothioate) has been found to have improved herbicidal properties in contrast to the trans isomer alone. Preferably the mixture contains at least about 20%, most preferably between about 60 and about 65%, of the cis isomer.

The S-isopropyl-1-(5-ethyl-2-methylpiperidinecarbothioate) having a desired amount of cis isomer can be produced by a two-step process comprising hydrogenation of 2-methyl-5-ethyl pyridine using a catalyst comprising rhodium supported on activated carbon to produce 2-methyl-5-ethyl piperidine and reacting the piperidine with isopropyl chlorothiolformate.

1 Claim, No Drawings

HERBICIDAL EFFECT OF A MIXTURE OF CIS AND TRANS ISOMERS OF S-ISOPROPYL-1-(5-ETHYL-2-METHYL-PIPERIDINECARBOTHIOATE)

This is a division of application Ser. No. 617,908, filed Sept. 29, 1975, now abandoned.

BACKGROUND AND PRIOR ART

British Pat. No. 1,236,875 discloses the herbicidal utility of a number of S-alkyl substituted 1-(disubstituted piperidine carbothioates) including S-isopropyl-1-(5-ethyl-2-methylpiperidine carbothioate), which is included in that patent as compound No. 4. As stated in the British patent, the piperidinyl ring is a rigid structural system and therefore the compounds described therein may exist in various stereochemical conformations, particularly cis and trans configurations.

As shown in the British patent, the compounds of this type had been found to be effective herbicides. S-isopropyl-1-(5-ethyl-2-methylpiperidine carbothioate) had been found to be a particularly effective herbicide and tests showing its herbicidal activity had been conducted, both on a small screen basis, and in cotton fields. Results of these tests are on pages 6 and 7 of the British patent.

It has now been found that the herbicidal activity of this compound is affected by the presence or absence of its cis isomer. More specifically, it has been found that the herbicidal effect of a mixture of cis and trans isomers of S-isopropyl-1-(5-ethyl-2-methylpiperidine carbothioate), preferably one containing at least about 20% of the cis isomer, and most preferably containing between about 60 and about 65% of the cis isomer, is remarkably and unexpectedly different from that of the trans isomer alone.

A method of using such a formulation comprises applying an herbicidally effective amount thereof to the area where control is desired. Such a formulation has been found to be especially effective in the control of undesirable vegetation in the presence of specific beneficial vegetation, especially in the presence of cotton.

An herbicide as used herein means a substance which controls or modifies the growth of plants. By an herbicidally effective amount is meant an amount of substance which causes a modifying effect upon the growth of plants. Such modifying effects include all deviations from natural development, for example, killing, retardation, defoliation, desiccation, regulation, stunting, tillering, stimulation, dwarfing and the like. By "plants" is meant germinant seeds, emerging seedlings and established vegetation including the roots and above-ground portions.

SUMMARY OF THE INVENTION

In one aspect this invention relates to a composition of matter comprising a mixture of cis and trans isomers of S-isopropyl-1-(5-ethyl-2-methylpiperidine carbothioate), preferably one containing at least about 20% of the cis isomer thereof, most preferably one containing between about 60 and about 65% of the cis isomer thereof.

In another aspect this invention relates to a method of controlling undesirable vegetation which comprises applying to the area where control of such vegetation is desired, an herbicidally effective amount of a composition comprising a mixture of cis and trans isomers of S-isopropyl-1-(5-ethyl-2-methylpiperidine carbothioate), preferably one containing at least about 20% of the cis isomer thereof, most preferably between about 60 and about 65%.

In a third aspect, this invention relates to a process for producing a composition comprising a mixture of cis and trans isomers of S-isopropyl-1-(5-ethyl-2-methyl-piperidine carbothioate) comprising:
(a) reacting 2-methyl-5-ethyl pyridine with hydrogen in the presence of a catalyst comprising rhodium supported on activated carbon to produce a product comprising a mixture of cis and trans isomers of 2-methyl-5-ethylpiperidine; and
(b) reacting the product obtained from step (a) with isopropyl chlorothiolformate to produce S-isopropyl-1-(5-ethyl-2-methylpiperidine carbothioate).

In a fourth aspect, this invention relates to the production of a mixture of cis and trans isomers of the intermediate 2-methyl-5-ethylpiperidine by the process of step (a) above.

In a fifth aspect, this invention relates to a process for producing a composition comprising a mixture of cis and trans isomers of S-isopropyl-1-(5-ethyl-2-methyl-piperidine carbothioate) comprising reacting isopropyl chlorothiolformate with a stoichiometric excess of a mixture of cis and trans isomers of 5-ethyl-2-methyl-piperidine in the presence of an inert diluent.

DETAILED DESCRIPTION OF THE INVENTION

It has been found that a composition comprising a mixture of cis and trans isomers of S-isopropyl-1-(5-ethyl-2-methylpiperidine carbothioate) has an improved herbicidal effect as compared to the trans isomer alone, at low rates of treatment, with respect to certain weeds. Preferably the mixture contains at least about 20% of the cis isomer most preferably between about 60 and about 65%.

Various methods can be used to produce a mixture of cis and trans isomers of S-isopropyl-1-(5-ethyl-2-methylpiperidine carbothioate), and these methods can be generally controlled so as to produce a mixture having a desired proportion of such isomers. For example, it has been found that commercially available lots of 2-methyl-5-ethylpiperidine from different sources can have different cis/trans ratios and that in general, the reaction between the 2-methyl-5-ethyl piperidine and isopropyl chlorothiolformate will result in a product having approximately the same cis/trans ratio as the starting piperidine. Alternatively, as described below, it has been found that the amount of cis isomer can be increased by conducting the reaction in the presence of an excess of the piperidine and by dilution of the reaction mixture.

If the intermediate piperidine is to be produced by hydrogenation of 2-methyl-5-ethylpyridine, as discussed below, the hydrogenation may be carried out under various conditions so as to produce a piperidine having a desired cis/trans isomer ratio, and that piperidine reacted as above, either with or without further changes in the cis/trans ratio, as desired.

Another method of obtaining a final product having a desired cis/trans ratio is by fractionation of the cis and trans isomers of the piperidine. This is advantageously performed by the method of Levy et al., Chem. Ber. 29, 1959 (1896), in which the piperidine is converted to its hydrochloride and the hydrochlorides of the two isomers are separated by fractional crystallization.

The hydrogenation of 2-methyl-5-ethylpyridine to 2-methyl-5-ethylpiperidine in the presence of a catalyst comprising rhodium supported on activated carbon is generally conducted at a temperature between about 50° C. and about 250° C., with pressures ranging from between about 50 to about 5000 psig. The reaction is generally completed within about three hours. It is necessary to maintain an excess of hydrogen during the reaction in order to avoid deactivation of the catalyst. Operation of the hydrogenation process at a temperature of about 110° C. and a pressure of between 100 and about 230 psig resulted in a product containing between about 60 and about 65% of the cis isomer.

A product having a higher cis content can be produced by conducting the process at a higher pressure and lower temperature within the foregoing ranges. Conversely, operation at higher temperatures would produce a product having a higher trans content. For instance, it was found that operation at over 200° C. results in a product having nearly 80% of the trans isomer. Operation at such temperatures also permits the use of a substantially smaller amount of catalyst than at 110° C., and the catalyst could also be used for several runs without being deactivated.

It has also been found that the cis/trans ratio of the final product S-isopropyl-1-(5-ethyl-2-methylpiperidine carbothioate) is not necessarily fixed by that of the intermediate piperidine. The cis isomer of the piperidine reacts more rapidly with isopropyl chlorothiolformate than does the trans isomer, particularly in a dilute medium. Consequently, the content of cis isomer in the final product can be thus increased by conducting the reaction in the presence of a stoichiometric excess of the cis isomer, preferably in the presence of an inert diluent such as ethyl ether, benzene, toluene or similar organic solvents which are inert towards the reactants or reaction products. The piperidine may be used in an excess of between about 50 and about 300%. The greater the excess used, the greater will be the increase in cis content. Generally, the effect of additional excess of the piperidine decreases markedly at greater than 100% excess and no increase in effect is seen at over 300% excess. Temperatures are preferably below room temperature, most preferably between about −5° C. and −10° C.

A number of compositions comprising various cis/trans ratios of S-isopropyl-1-(5-ethyl-2-methylpiperidine carbothioate) were prepared as described in the following Examples and were subjected to herbicidal testing as described following the Examples. The Examples herein are only intended to represent some of the many possible cis and trans mixtures of S-isopropyl-1-(5-ethyl-2-methylpiperidine carbothioate) which can be used in accordance with this invention, and only some of the techniques for preparing such compositions. The invention, therefore, is only considered to be limited by the claims which appear at the end of this application.

EXAMPLE 1

132 g. (3.30 mole) of sodium hydroxide dissolved in 2,000 cc of water was introduced into a 5-liter flask. 419.8 g. (3.30 moles) of 5-ethyl-2-methylpiperidine obtained from a commercial source and having a cis/trans isomer ratio of 44/56 (analyzed by gas chromatography) was added. The mixture, which was heterogeneneous, was cooled in an ice bath to 5.5° C., then 415.8 g. (3 moles) of isopropyl chlorothiolformate was added with partial dry-ice cooling. The addition was complete after about 1 hour, at which point the temperature was about 12° C.

The mixture was heated to 68° over the next hour and was then phase separated while still warm. The organic phase was cooled to room temperature and washed with two 500 cc portions of dilute hydrochloric acid (50 cc of conc. hydrochloric acid made up to 500 cc with water) and two 500 cc portions of water. The product was dried over anhydrous magnesium sulfate and then filtered from the salt. There was obtained 630.7 g. (91.6 percent of theoretical) of S-isopropyl-1-(5-ethyl-2-methylpiperidine carbothioate), $n_D^{30}$ 1.4966. This product consisted of 44% of the cis isomer and 56% of the trans isomer.

EXAMPLE 2

In order to obtain a product having a high content of cis isomer, the following procedure was used:

88.0 g. (2.20 moles) of sodium hydroxide dissolved in 2000 cc of water was introduced into a 12 l. flask. 508.9 g (4.00 moles) of 5-ethyl-2-methylpiperidine having a cis/trans isomer ratio of 60.5/39.5 (analyzed by gas chromatography) in 6 l. of ethyl ether was added. The heterogeneous mixture was cooled in a dry-ice - isopropanol bath to −7° C. and then 277.2 g. (2.00 moles) of isopropyl chlorothiolformate was added over an interval of 14 minutes at a temperature range of −7° to −4° C. The cooling bath was then removed and the flask was placed in a warm water bath so that the ether was brought to reflux at a temperature of 37° C. The mixture was refluxed for 2 hours and was then phase separated. The ether phase was washed with four 2 l. portions of ice cold dilute hydrochloric acid (400 cc of conc. hydrochloric acid made up to 2 l. with ice and water) and two 2 l. portions of water. The solution was then dried over anhydrous magnesium sulfate, filtered and the solvent was removed under reduced pressure on a rotary evaporator. The last traces of solvent were removed under high vacuum with a maximum bath temperature of 65° C. and minimum pressure of 120 microns. There was obtained 433.1 g. (94.4% yield) of S-isopropyl-1-(5-ethyl-2-methylpiperidine carbothioate), $n_D^{30}$ 1.4960. This product consisted of 88.8% cis and 11.2% trans isomers.

EXAMPLE 3

In order to obtain a product having a high content of trans isomer it was necessary to first fractionally crystallize the 5-ethyl-2-methylpiperidine hydrochloride.

636 g. (5.00 moles) of 5-ethyl-2-methylpiperidine which contained 65–70% trans isomer was dissolved in 2500 cc of acetone and was charged to a 5 l. flask. 109 g. (3.00 moles) of anhydrous hydrogen chloride was then added at a temperature range of 26°–55° C. with cooling. The thick mixture was cooled to 24° C. and filtered. The cake was slurried three times with 1 l. portions of acetone and dried. There was obtained 438 g. (89.2% yield) of trans 5-ethyl-2-methylpiperidine hydrochloride, m.p. 174.5°–175.5° C. This product was essentially 100% trans isomer.

The amine hydrochloride was converted to the thiocarbamate product in the following manner:

1092 g. (27.3 moles) of sodium hydroxide dissolved in 4 l. of water was charged to a 12 l. flask. 2245 g. (13.7 moles) of trans-5-ethyl-2-methylpiperidine hydrochloride was then added with ice cooling. 1802 g. (13.0 moles) of isopropyl chlorothiolformate was then added with ice cooling over an interval of 1 hour maintaining the temperature between 20°–26° C. The reaction mixture was then heated to 51° C. and held at that temperature for 2 hours. The stirring was then stopped and the mixture was allowed to phase separate. The aqueous phase was removed and the product was washed twice with 4 l. portions of 16.7% salt solution. The excess amine was removed by steam distillation. The wet product was dried by shaking with 3 heaping teaspoons each of anhydrous magnesium sulfate and Celite Filter Aid. ® After filtering, there was obtained 2668 g. (89.5% yield) of S-isopropyl-1-(5-ethyl-2-methylpiperidine carbothioate), $n_D^{30}$ 1.4976. Gas chromatography showed that this product was 100% trans isomer and 99% pure.

EXAMPLE 4

This example illustrates the preparation of the intermediate 2-methyl-5-ethylpiperidine by hydrogenation of 2-methyl-5-ethylpyridine with a catalyst comprising rhodium supported on activated carbon.

1278 g. (10.55 moles) of 2-methyl-5-ethylpyridine was placed in an autoclave. The autoclave was pressured with argon to 40 pounds, the contents heated to about 100° C. and permitted to stand overnight to obtain temperature equilibrium. 63.9 g. of 5% rhodium supported on activated carbon was slurried with a portion of the pyridine starting material and added to the autoclave. A hydrogen pressure regulator was set to 100 pounds and the hydrogen was introduced into the autoclave. The reaction was mildly exothermic. When the temperature reached 110° C. a slow flow of cooling water was passed through a cooling coil surrounding the autoclave. This was sufficient to maintain a constant temperature during the initial phase of the reaction. After the reaction was about one-half completed (as evident by a pressure drop on the hydrogen cylinder gauge), the pressure was increased to 200 pounds. When the temperature of the reaction mixture was observed to be decreasing, the cooling water was turned off. As the reaction neared completion the temperature began to drop down to 100° C. The total reaction time was about 2 hours and 20 minutes. There was obtained 1264 g. of product (94.2% of theoretical), $n_D^{30}$ 1.4448. Analysis by gas chromatography showed a cis/trans isomer ratio of about 60/40.

Other runs conducted in the same manner resulted in mixtures of cis and trans isomers containing between about 60 and about 65% cis isomer and correspondingly between about 35 and about 40% trans isomer.

The 2-methyl-5-ethylpiperidine obtained in this fashion was reacted with isopropyl chlorothiolformate in a manner similar to that in Example 1 and produced a final product having the cis/trans ratio of the intermediate.

A number of batches of S-isopropyl-1-(5-ethyl-2-methylpiperidine carbothioate) containing different amounts of cis and trans isomers, ranging from 100% trans to 90% cis, were prepared by processes as described in Examples 1 through 4. The batches are hereinafter referred to by their letter designations corresponding to cis/trans ratios as follows.

Table 1

| Batch | Cis/trans ratio |
| --- | --- |
| A | 44/56 |
| B | 45/55 |
| C | 85/15 |
| D | 0/100 |
| E | 63/37* |
| F | 90/10 |
| G | 24/76 |
| H | 89/11 |
| I | 0/100 |
| J | 22/78 |

*Average cis/trans ratio of the combined products of various runs in which the cis content ranged between about 60 and about 65%.

HERBICIDAL EVALUATION TESTS

Herbicidal evaluation tests using pre-plant incorporation of different batches of isomeric mixtures or, in some cases the pure trans isomer, of S-isopropyl-1-(5-ethyl-2-methylpiperidine carbothioate) show that for a number of plants, especially weeds or other undesirable vegetation, the effect of different isomeric mixtures and of the 100% trans isomer of this compound is basically the same. That is, at various levels of treatment, the various batches A through J either were equally effective or ineffective against selected weeds. However, with respect to certain weeds there was a substantial difference in effect at low levels, generally 1.5 pounds per acre or less, between those batches which contained some cis isomer and those batches which contained only the trans isomer. In addition, a mixture of isomers containing between about 60 and about 65% of the cis isomer showed less tendency to cause stunting of the cotton than a mixture of isomers having a substantially lower (22%) cis content. Stunting of cotton, within the first two weeks of its growth is considered an undesirable event as it appears to be related to root pruning (i.e., poor development) of the lateral feed root system, even though the stunting may itself disappear with time.

More particularly, all the batches above were very herbicidally effective against foxtail, crabgrass, watergrass, signalgrass and carpetweed. However, as can be seen from the test results which follow, marked differences were apparent at low treatment levels with respect to shattercane, certain wild oats, purslane, and nutsedge. All numbers in the tables represent percent control on a scale from 0 (representing no injury) to 100 (representing complete kill).

TEST 1

Comparative tests were performed on various batches as indicated below, pre-plant incorporated in loamy sand in 8 × 12 × 3 metal flats at rates of ½ and 1 pound per acre on watergrass, foxtail, crabgrass, milo, oats, nutsedge and pigweed. Results of these tests are shown in Table 1.

Table 1

| Batch Cis/Trans Ratio | | Water-grass | | Foxtail | | Crab-grass | | Milo | | Oats | | Nut-sedge | | Pig-weed |
| --- | --- | --- | --- | --- | --- | --- | --- | --- | --- | --- | --- | --- | --- | --- |
| Cis | Trans | | | | | | | Treatment, rate, lb/acre | | | | | | |
| % | % | ½ | 1 | ½ | 1 | ½ | 1 | ½ | 1 | ½ | 1 | ½ | 1 | 1 |
| 45 | 55 | 70 | 80 | 90 | 95 | 60 | 95 | 0 | 80 | 95 | 98 | 0 | 50 | 0 | 0 |
| 85 | 15 | 60 | 80 | 90 | 95 | 60 | 95 | 0 | 80 | 95 | 98 | 0 | 50 | 0 | 0 |
| 0 | 100 | 70 | 80 | 90 | 95 | 60 | 90 | 0 | 40 | 60 | 80 | 0 | 20 | 0 | 0 |
| 63* | 37* | 60 | 80 | 90 | 95 | 50 | 95 | 0 | 90 | 95 | 98 | 0 | 50 | 0 | 0 |
| 90 | 10 | 50 | 70 | 90 | 95 | 60 | 90 | 0 | 70 | 80 | 90 | 0 | 50 | 0 | 0 |
| 24 | 76 | 70 | 80 | 90 | 95 | 40 | 90 | 0 | 70 | 80 | 95 | 0 | 20 | 0 | 0 |

Table 1-continued

| Batch Cis/Trans Ratio | | Water-grass | | Foxtail | | Crab-grass | | Milo | | Oats | | Nut-sedge | | Pig-weed |
|---|---|---|---|---|---|---|---|---|---|---|---|---|---|---|
| Cis | Trans | | | | | | | Treatment, rate, lb/acre | | | | | | |
| % | % | ½ | 1 | ½ | 1 | ½ | 1 | ½ | 1 | ½ | 1 | ½ | 1 | 1 |
| 89 | 11 | 60 | 80 | 90 | 95 | 50 | 95 | 0 | 80 | 95 | 99 | 0 | 50 | 0 | 0 |
| 0 | 100 | 70 | 80 | 90 | 95 | 60 | 90 | 0 | 30 | 90 | 95 | 0 | 10 | 0 | 0 |
| Average | | | | | | | | | | | | | | | |

Thus, the different batches had essentially the same effect on watergrass, foxtail, crabgrass and pigweed. None of the batches showed a herbicidal effect on nutsedge at ½ lb. per acre. However, when tested at 1 pound per acre, the 100% trans batches D and I and the 76% trans batch 6 were markedly less effective against nutsedge than the remaining batches.

TEST 2

Batches C and D, containing respectively 85% cis and 100% trans isomer, were compared with respect to cotton and a number of different weeds at levels ranging from 0.5 to 8.0 pounds per acre. Stock solutions were formulated and preplant incorporated in loamy soil in 8 × 12 × 3 flats as in Test 1. With respect to cotton, neither batch proved phytotoxic at two pounds or less per acre. Both batches had a phytotoxic effect on cotton of about 20% at 4 pounds and above. Both batches behaved approximately the same with respect to watergrass and nutsedge. However, as can be seen from the following results, batch C, having a high cis content, was more effective against pigweed in general, and against foxtail at low rates (0.5 and 1 pound per acre) than bath D (100% trans).

Table 2

| Batch | Rate lb./A | Per Cent Control | |
|---|---|---|---|
| | | Pigweed | Foxtail |
| C | 0.5 | 0 | 70 |
| | 1.0 | 0 | 95 |
| | 2.0 | 50 | 98 |
| | 4.0 | 80 | 100 |
| | 8.0 | 90 | 100 |
| D | 0.5 | 0 | 50 |
| | 1.0 | 0 | 70 |
| | 2.0 | 50 | 95 |
| | 4.0 | 60 | 100 |
| | 8.0 | 70 | 100 |

TEST 3

Different isomeric mixtures of cis and trans isomers were formulated and tested against cocklebur, hairy crabgrass, Florida purslane and sicklepod. The tests were conducted by pre-plant incorporation of 3 pounds of each mixture of cis and trans isomers in a cotton field in which the above weeds were also present. Test results are summarized in Table 3.

Table 3

| cis-trans ratio | Cotton Injury % | Weed Control % | | | |
|---|---|---|---|---|---|
| | | Florida purslane | Cockle-bur | Hairy crabgrass | Sickle-pod |
| 23:77 | 0 | 50 | 0 | 99 | 0 |
| 50:50 | 0 | 50 | 0 | 99 | 0 |
| 77:23 | 0 | 80 | 0 | 99 | 0 |

As can be seen, good protection was obtained at all cis/trans ratios against hairy crabgrass, no batches had any effect against cocklebur or sicklepod, and the effect on Florida purslane was only fair except at a high ratio of cis to trans (77% cis).

TEST 4

Comparative greenhouse tests were performed on batches E, F and I, having respectively 63 (average), 90, and 0 percent of the cis isomer. Tests were conducted at rates ranging from 0.75 to 6.0 pounds per acre and were conducted similarly to tests 1 and 2. Results of these tests are shown in the following table 4.

Table 3

| Batch | cis/trans Ratio | Rate lb/A | Percent Weed Control | | | | | | | Crop Phytotoxicity | | |
|---|---|---|---|---|---|---|---|---|---|---|---|---|
| | | | Barley % | Foxtail % | Water-grass % | Wild Oats % | Shatter-cane % | Nutsedge % | Average % | Cotton % | Corn % | Sugar Beets % |
| H | 63:37 | 0.75 | 50 | 60 | 70 | 80 | 70 | 20 | 58 | 0 | — | — |
| | | 1.5 | 95 | 70 | 80 | 100 | 90 | 70 | 84 | 10 | — | — |
| | | 3.0 | — | — | — | — | — | 95 | — | 25 | 60 | 40 |
| | | 6.0 | — | — | — | — | — | 100 | — | 30 | 75 | 70 |
| | 90:10 | 0.75 | 60 | 50 | 60 | 80 | 80 | 30 | 60 | 0 | — | — |
| | | 1.5 | 90 | 60 | 80 | 95 | 90 | 60 | 79 | 20 | — | — |
| | | 3.0 | — | — | — | — | — | 85 | — | 30 | 50 | 30 |
| | | 6.0 | — | — | — | — | — | 100 | — | 30 | 70 | 80 |
| I | 0:100 | 0.75 | 10 | 40 | 60 | 20 | 20 | 10 | 20 | 0 | — | — |
| | | 1.5 | 50 | 60 | 80 | 90 | 70 | 30 | 70 | 10 | — | — |
| | | 3.0 | — | — | — | — | — | 70 | — | 20 | 50 | 10 |
| | | 6.0 | — | — | — | — | — | 90 | — | 30 | 75 | 30 |

Injury ratings were taken 17 days after treatment; phytotoxicity ratings 38 days after treatment. From these results it can be seen that:

With respect to wild oats, batches E and F, containing cis isomer, were far more effective at the low rate of 0.75 pounds per acre than was batch I, which represented 100% trans isomer. Slightly more effect was also shown at 1.5 pounds per acre.

With respect to shattercane, batches E and F, containing cis isomer, were more effective at levels of 1.75 and 1.5 pounds per acre than was batch I.

With respect to nutsedge, batches E and F were far more effective than batch I until the treatment rate reached 6 pounds per acre, at which point batches E and F were only slightly more effective than batch I.

With respect to cotton, all batches show approximately equal phytotoxicity, although batch F was slightly more phytotoxic.

These results show that a mixture of cis and trans isomers can be used at a rate of 0.75 pounds per acre and be quite effective in eliminating shattercane, wild oats, watergrass, and still be effective against foxtail and nutsedge, without affecting a cotton crop. On the other hand, it would be necessary to use a higher rate of application of a mixture containing less than 20% cis isomer, or of the trans isomer alone, to achieve similar results.

TEST 5

Comparative field tests were performed on batches E, F and J, having respectively, 63 (average), 90 and 22% of the cis isomer. Tests were conducted at 3, 4 and 5 lbs/acre by preplant incorporation into fields of cotton and sugar beets planted in sandy loam soil in the presence of a number of weeds. Test results were observed after 30 and after 60 days, respectively.

Results on stunting of cotton observed after 30 days showed:

Table 5

| Batch | Rate, lb/acre | Cotton Stunting, % |
|---|---|---|
| E | 3 | 0 |
| F | 3 | 0 |
| J | 3 | 5 |
| E | 4 | 5 |
| F | 4 | 0 |
| J | 4 | 10 |
| E | 5 | 10 |
| F | 5 | 0 |
| J | 5 | 15 |

Comparative tests with two standard cotton herbicides, Cotoran® 80W and Treflan® 4E, applied at their recommended rates (1¼ and 0.75 lb/acre respectively) showed stunting of 15 and 10% respectively.

Results on weed control observed after 60 days are given in Table 6.

Table

| Batch | Rate, lb/acre | Goose-grass | Johnson-grass | Tea-weed | Pig-weed | Morning glory |
|---|---|---|---|---|---|---|
| E | 3 | 96 | 96 | 85 | 85 | 90 |
| F | 3 | 96 | 96 | 80 | 80 | 90 |
| J | 3 | 98 | 98 | 90 | 90 | 90 |
| E | 4 | 98 | 98 | 90 | 90 | 90 |
| F | 4 | 98 | 98 | 85 | 85 | 90 |
| J | 4 | 98 | 98 | 90 | 90 | 90 |
| E | 5 | 99 | 99 | 95 | 95 | 95 |
| F | 5 | 99 | 99 | 95 | 95 | 95 |

Table-continued

| Batch | Rate, lb/acre | Goose-grass | Johnson-grass | Tea-weed | Pig-weed | Morning glory |
|---|---|---|---|---|---|---|
| J | 5 | 99 | 99 | 95 | 95 | 95 |

Results on sugar beets taken at 30 days show the following stand counts:

Table 7

| Batch | Rate, lb/acre | Stand count |
|---|---|---|
| E | 3 | 101 |
| F | 3 | 99 |
| J | 3 | 92 |
| E | 4 | 108 |
| F | 4 | 85 |
| J | 4 | 93 |
| E | 5 | 92 |
| F | 5 | 103 |
| J | 5 | 94 |
| Cotoran $^R$ 80W | 1.5 | 0 |
| Treflan $^R$ 45 | 0.75 | 0 |
| Untreated control | — | 49 |

From the results above, it can be seen that:
(a) Batch J, containing 22% cis isomer gave somewhat better weed control than the other two batches but was also more injurious to cotton at all levels tested.
(b) Batch F, containing 90% cis isomer, did not injure cotton at all levels tested but was also generally least effective against weeds.
(c) All three batches showed, however, at least good activity against weeds.
(d) All three batches showed less stunting of cotton than the comparable standard herbicides.
(e) All three batches showed at least good activity against weeds while leaving sugar beets substantially unaffected.
(f) Batch F, containing between about 60 and about 65% of the cis isomer, showed the best combination of weed control and non-injury of cotton, at all three levels of treatment.

What is claimed is:
1. A method of selectively controlling undesirable vegetation with respect to cotton by applying to the vegetation or the habitat thereof, a herbicidal composition of matter comprising a herbicidally effective amount of a mixture of cis and trans isomers of S-isopropyl-1-(5-ethyl-2-methylpiperidinecarbothioate) containing between about 60 and 65% of the cis isomer.

* * * * *

UNITED STATES PATENT AND TRADEMARK OFFICE
CERTIFICATE OF CORRECTION

PATENT NO. : 4,119,431
DATED : October 10, 1978
INVENTOR(S) : Harry Tilles

It is certified that error appears in the above—identified patent and that said Letters Patent are hereby corrected as shown below:

Column 10, lines 22 and 23, "someh-wat" should read -- some-what --.

Signed and Sealed this

Eighteenth Day of September 1979

[SEAL]

Attest:

LUTRELLE F. PARKER

*Attesting Officer*  *Acting Commissioner of Patents and Trademarks*

UNITED STATES PATENT AND TRADEMARK OFFICE
CERTIFICATE OF CORRECTION

PATENT NO. : 4,119,431
DATED : October 10, 1978
INVENTOR(S) : Harry Tilles

It is certified that error appears in the above-identified patent and that said Letters Patent are hereby corrected as shown below:

Columns 7 and 8, "Table 3", line 33, should read "Table 4".

Columns 7 and 8, Table 3, line 33, corrected to Table 4 under Batch, "H" should read "E", and "F" should be inserted before ratio of 90:10.

Signed and Sealed this

Twenty-fifth Day of March 1980

[SEAL]

Attest:

SIDNEY A. DIAMOND

Attesting Officer    Commissioner of Patents and Trademarks